United States Patent [19]
Trott

[11] Patent Number: 5,474,565
[45] Date of Patent: * Dec. 12, 1995

[54] ENDOSCOPIC SUTURING NEEDLE

[75] Inventor: A. Frank Trott, Largo, Fla.

[73] Assignee: Linvatec Corporation, Largo, Fla.

[*] Notice: The portion of the term of this patent subsequent to May 17, 2011, has been disclaimed.

[21] Appl. No.: 152,468

[22] Filed: Nov. 12, 1993

Related U.S. Application Data

[63] Continuation of Ser. No. 914,810, Jul. 16, 1992, Pat. No. 5,312,422.

[51] Int. Cl.⁶ .................................. A61B 17/04
[52] U.S. Cl. ..................... 606/144; 606/139; 128/898
[58] Field of Search ............................. 606/144–148, 606/139; 128/898

[56] References Cited

U.S. PATENT DOCUMENTS

| 17,272 | 5/1857 | Garvey. |
|---|---|---|
| 234,371 | 11/1880 | Benjamin. |
| 371,141 | 10/1887 | Hutchinson. |
| 411,136 | 9/1889 | Swem. |
| 591,403 | 10/1897 | Hoffmann. |
| 790,120 | 5/1905 | Garrett. |
| 1,545,682 | 7/1925 | Nelson. |
| 1,583,271 | 5/1926 | Biro. |
| 1,822,330 | 9/1931 | Ainslie. |
| 2,264,679 | 12/1941 | Ravel. |
| 2,457,379 | 12/1948 | Kallenbach. |
| 2,579,192 | 12/1951 | Kohl. |
| 2,738,790 | 3/1956 | Todt et al.. |
| 3,372,477 | 3/1968 | Hoppe. |
| 3,877,434 | 4/1975 | Ferguson et al.. |
| 4,372,302 | 2/1983 | Akerlund. |
| 4,614,187 | 9/1986 | Mulhollan et al.. |
| 4,779,616 | 10/1988 | Johnson. |
| 5,015,250 | 5/1991 | Foster. |
| 5,059,201 | 10/1991 | Asnis. |
| 5,084,058 | 1/1992 | Li. |
| 5,149,329 | 9/1992 | Richardson. |

FOREIGN PATENT DOCUMENTS

| 2305815 | 8/1974 | Germany ........................ 606/138 |
|---|---|---|
| 2532242 | 2/1977 | Germany. |

OTHER PUBLICATIONS

The Journal of Arthroscopic and Related Surgery, vol. 9, No. 2, "Arthroscopic Meniscus Repair: The Easy Way", 1993.

Primary Examiner—Gary Jackson
Attorney, Agent, or Firm—Rosenblatt & Associates

[57] ABSTRACT

A suturing needle is illustrated which can engage a suture to an outer housing, thereby presenting a relatively smooth surface at the distal end of the apparatus to minimize tissue trauma. A lock feature prevents unexpected extension of the needle from the outer housing which could release the suture. A finger switch is used to overcome the locking mechanism when it is desired to release the suture. The distal end of the housing and the needle are a generally similar flat profile to minimize uneven edges which could damage the tissue. The suture is retained in a hook located in the needle, the opening for which is retracted in the housing to retain the suture.

11 Claims, 2 Drawing Sheets

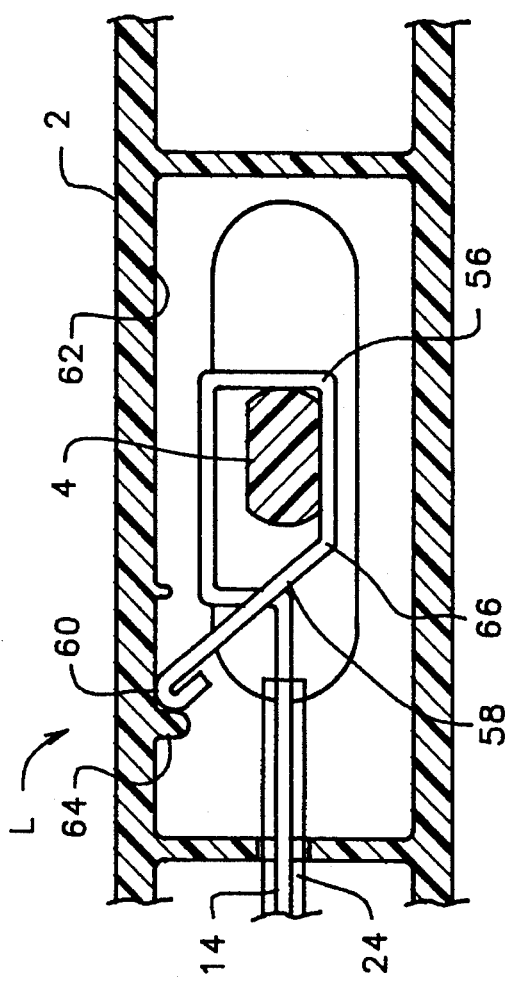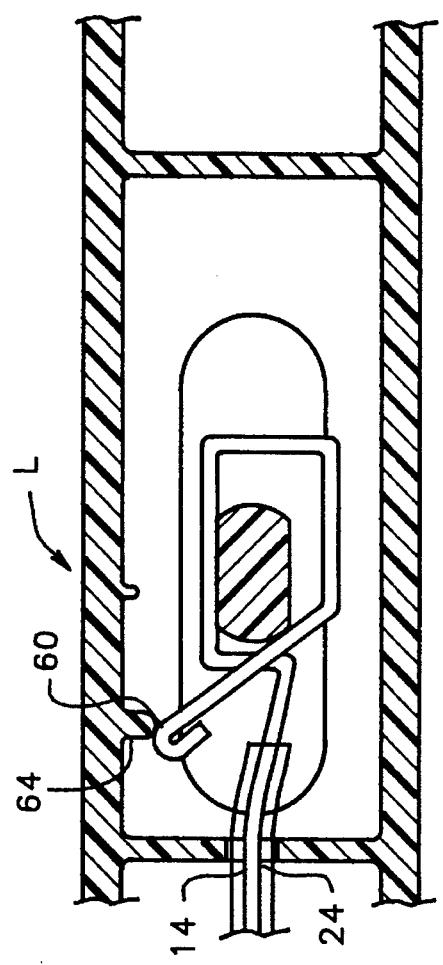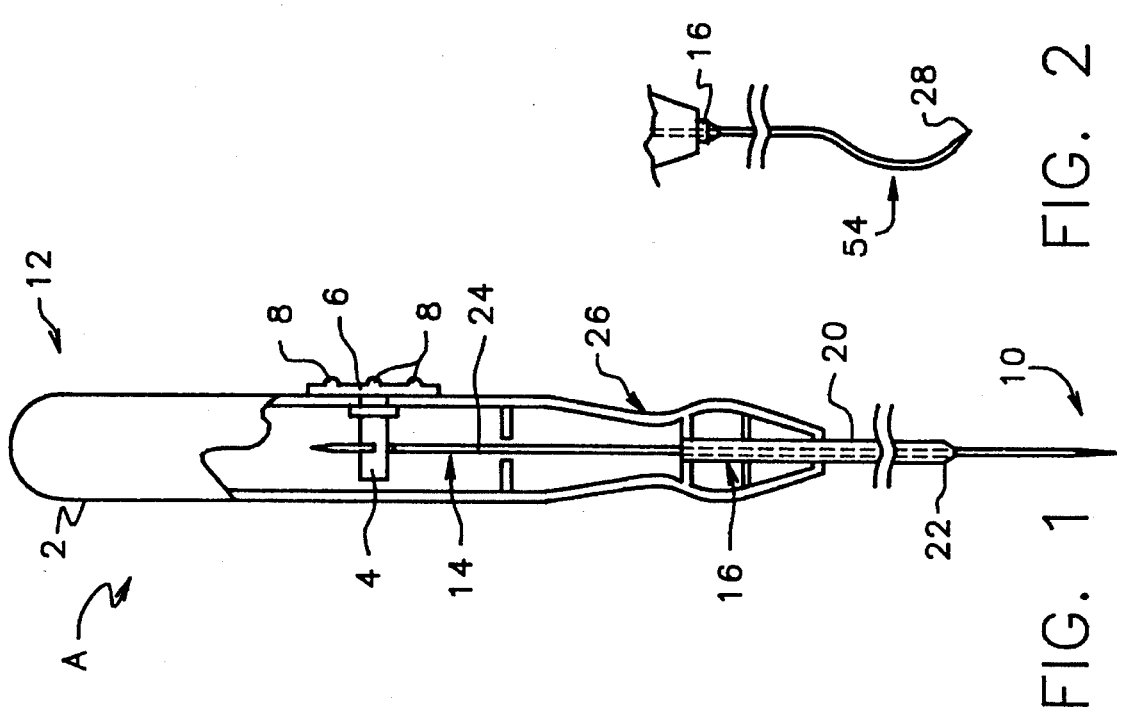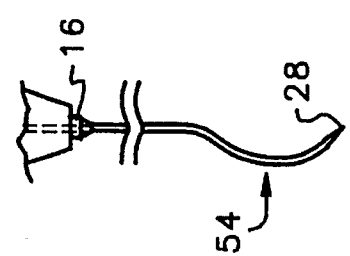

ENDOSCOPIC SUTURING NEEDLE

This application is a continuation of application Ser. No. 07/914,810, filed Jul. 16, 1992, now U. S. Pat. No. 5,312,422.

FIELD OF THE INVENTION

This invention relates generally to the field of medical instruments and more particularly to an endoscopic suturing needle that is used to insert a suture within the body of a human being or of an animal.

BACKGROUND OF THE INVENTION

Manually operated medical and surgical instruments provide surgeons with the capability of emplacing or removing sutures. Some of the devices enable surgeons to grasp suture needles within the procedural field. These instruments have jaws at the distal end, which allow the needle to be trapped and removed. Surgeons utilize these various devices when there is limited accessibility within the procedural field. To alleviate large incisions, which involve a higher morbidity due to increased trauma to surrounding tissue and a higher incidence of complications, endoscopic procedures have become preferable methods of accessing various surgical sites. The suture devices are utilized in endoscopic procedures in order to achieve hemostasis after the removal or biopsy of an organ.

The instruments that are typically used to suture tissue in these confined sites are needles inserted through a trocar sheath or devices in which a retractable needle is encased in a cannula. The needle on these devices typically penetrates entrapped tissue. The hook on the needle snares the sutures in the recess and the needle is retracted back through the tissue. These devices are bulky, and force is often necessary to engage the suture. Tissue can be dense and difficult to penetrate with a needle. In some of the instruments that are elongated to reach the surgical or biopsy site, the shaft and posts are not rigid enough to endure the force that must be applied to penetrate the tissue. Many times this force is necessary because the needle is not sharp enough to easily pierce the dense tissue. The instruments are sometimes heavy and burdensome, which restricts the surgeon's maneuverability and causes fatigue. Use of undue force in the suturing procedure retards healing, and large needle heads and cannulas restrict the physician's vision. Also, the instruments are often not sufficiently elongated to accommodate adequate retrieval or rotation of the suture material.

A known ligature provides a series of gauged needle sizes that allow suturing of tissue. However, these needles are used primarily in shoulder surgery due to the length of the devices. This ligature is designed with a sliding member that is unstable due to friction encountered during penetration into the tissue. The distal end of the ligature includes a recess that holds the suture in place. The friction encountered during penetration forces the recess open, exposing sharp edges that sever tissue. The prior art is not well suited for endoscopic surgery and cannot be adapted to these procedures without compromising the integrity of the stainless steel shaft and post on the instruments.

German Patent 2,532,242 illustrates a fixed rounded needle having an internal sleeve which is shiftable to engage a suture in a cut-out within the needle. However, the opening for entry of the suture remains exposed due to the track for the internal sleeve leaving notches open on the periphery of the stationary needle. These open notches can engage the tissue and cause trauma.

Accordingly, it is an object of this invention to provide surgeons with a device that minimizes trauma to tissue during the suturing procedure. The present invention provides a needle with a hook that recedes into a protective sheath, which allows accomplishment of the above objective.

SUMMARY OF THE INVENTION

The foregoing problems are solved and technical advances are achieved with this invention. Surgeons may use the present invention not only to emplace sutures into tissue, but sutures may be withdrawn with this device. A loop may then be tied and the process may be repeated until the desired stitching pattern is achieved. The suturing process may be completed with the use of the one instrument.

The endoscopic suturing needle of the present invention provides an improved elongated thin needle that increases the speed of the suturing procedure. The present invention is preferably approximately 11½" in length. The handle is preferably made of a lightweight plastic molded material. There is a thumb switch that slides forward on the handle that extends and retracts the suture needle assembly. The needle assembly extends from the handle through an outer tube. A stiffener tube is connected to the outer tube to ensure rigidity. The needle is angulated to achieve ease in suturing. The end of the outer tube is flattened and forms a protective sheath. The suture needle has a sharp tip and is 1.1 mm in length. There is a rounded hook that is approximately 4 mm from the tip of the needle. This hook evolves into a recess. The distal end of the hook recedes into the lumen of the protective sheath. This retraction capacity allows encasement of the suture prior to transversion of the tissue. After the suture is secured and loaded in place, the needle penetrates the tissue. Once optimal placement of the suture is attained, the thumb switch on the handle slides forward under pressure of the thumb, and the needle and hook extend out of the protective sheath. This disengages the hook on the needle and allows the suture to be easily released from the recess. The hook on the needle may then be re-engaged by retraction, thus assuring an eased withdrawal of the needle. This process is repeated to create the desired stitching pattern.

These and other objects and features will be apparent from the following detailed description when read in conjunction with the drawing figures.

BRIEF DESCRIPTION OF THE DRAWINGS

FIG. 1 is a sectional elevational view showing the assembly of the components of the apparatus of the present invention.

FIG. 2 is a detailed view of the distal tip, showing the curvature of the needle.

FIG. 8 is a sectional elevational view showing the needle detent system.

FIG. 9 is another view of the detent system shown in FIG. 8, showing how the detent is defeated.

DETAILED DESCRIPTION OF THE PREFERRED EMBODIMENT

Figure 3:
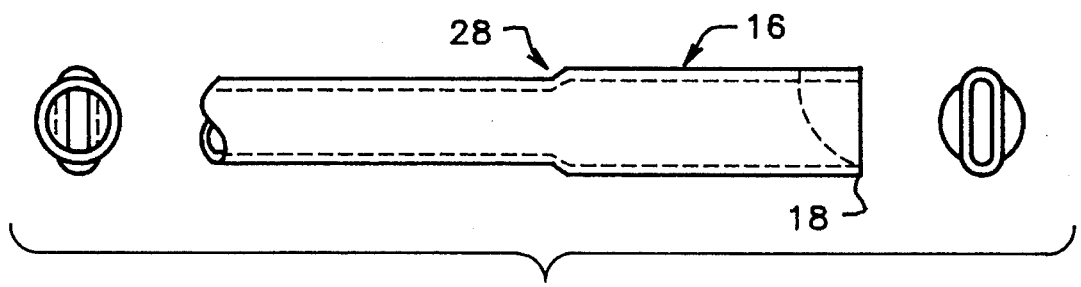
FIG. 3 is a detailed view of the distal end of the outer tube through which the needle extends, showing its changes in cross-sectional shape.

The apparatus A is shown in FIG. 1 in part section, It features an elongated handle 2 that can be made from a variety of lightweight materials so as to minimize fatigue for the surgeon in using the instrument. The handle 2 can be made in one piece or in several component pieces, In the preferred embodiment the handle 2 is hollow to accommodate push block 4, Push block 4 extends through handle 2 to a point where it is connected to thumb switch 6, Thumb switch 6 has a plurality of ridges 8 to minimize slippage in operation of the switch between its open and closed position. The open position of switch 6 is achieved by pushing it distally toward distal end 10. Conversely, the closed position is achieved by moving switch 6 towards proximal end 12.

Push block 4 is connected to an elongated needle assembly 14. This can be accomplished in various ways as shown in FIGS. 8 and 10. The needle assembly 14 extends through an inner tube 16. Inner tube 16 terminates at a distal end 18 (see FIG. 5). Inner tube 16 extends through outer tube 20, as shown in FIG. 1. The outer tube 20 extends from within handle 2 to a distal end 22, with inner tube 16 extending beyond distal end 22.

It should be noted that in operation of the apparatus of the present invention the outer tube 20 is stationary, as is the inner tube 16. The only moving parts are the switch 6 connected to push block 4, which is in turn connected to needle assembly 14. A loose tube 24 supported by handle 2 circumscribes needle assembly 14 and acts as an extension stop, as shown in FIG. 8.

The handle 2 has a depressed segment 26 to facilitate grip of the apparatus A while switch 6 is moved between open and closed positions. It should be noted that the profile of outer tube 20 to its distal end 22 is rounded. Similarly, the profile of inner tube 16, as it extends through the outer tube 20 and a portion beyond, is also rounded. Referring to FIG. 3, it can be seen that the profile of inner tube 16 changes near its distal end 18. At its distal end 18 the profile has been flattened and in cross-section has a generally race-track shape, as indicated in FIG. 7. At a transition 28, the profile of inner tube 16 changes to a rounded profile (FIGS. 5 and 6).

Figure 5:
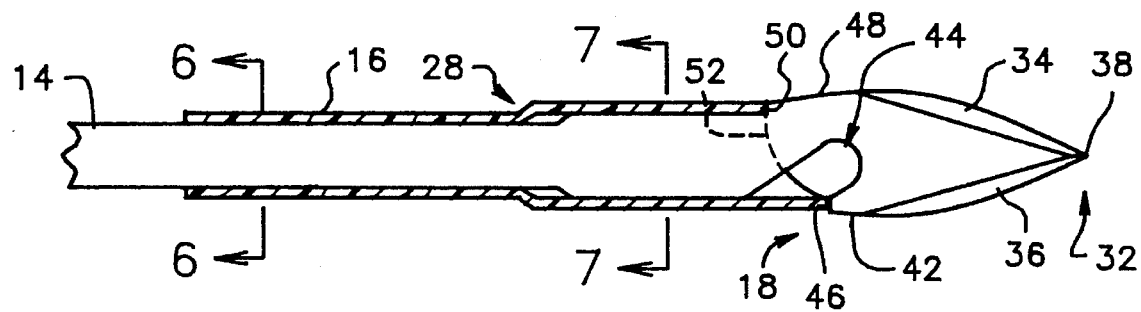
FIG. 5 is an assembly view showing the needle and how it fits beyond the outer sleeve.
Figure 6:
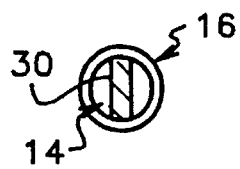
FIG. 6 is a sectional view along lines 6—6 of FIG. 6.
Figure 7:
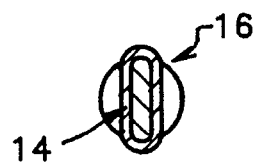
FIG. 7 is a sectional view along lines 7—7 of FIG. 6.

The nature of the fit between the needle assembly 14 and the is illustrated in FIGS. 5, 6, and 7. As seen in FIG. 5, at the point where section lines 6—6 appear, the profile of inner tube 16 is rounded, while the needle assembly 14 extending through at that portion is flat in a generally rectangular cross-section 30. After transition 28, the profile of inner tube 16 assumes the profile of the needle assembly, as shown in FIG. 7. The needle assembly 14 continues beyond distal end 18 of inner tube 16. The distal end 32 of the needle assembly 14 is illustrated in FIG. 5. There are a pair of sharpened edges 34 and 36 which lead to a tip 38. Proximally of the sharpened edges 34 and 36, the edges 40 and 42 are more rounded and dull.

Figure 4:
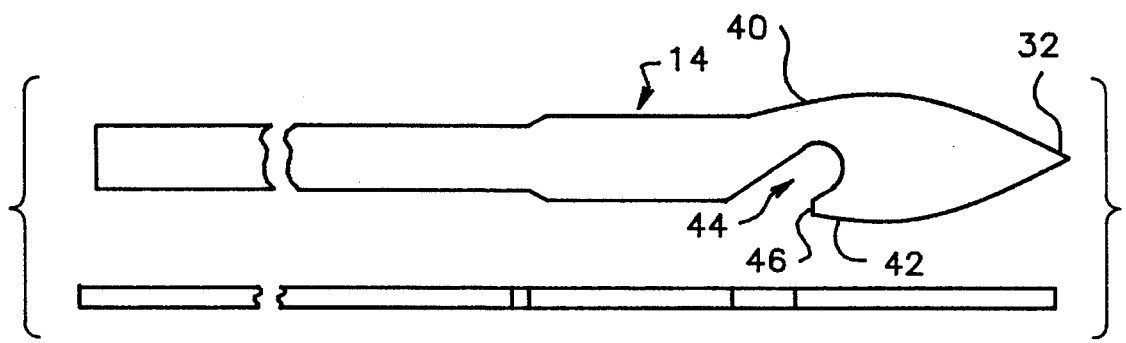
FIG. 4 is a detailed view of the distal end of the needle.

Referring now to FIG. 4, it can be seen that the needle assembly 14 has a recess 44 near its distal end 32. The recess 44 is adjacent and abutting the hook 46, which is disposed for contact with distal end 18 of inner tube 16 when the needle assembly is in the retracted position, as shown in FIG. 5. At the same time, while needle assembly 14 is retracted, a taper 48 also connects with edge 50 on inner tube 16 (see FIG. 5). Clearly the width of the distal end 32 of the needle assembly 14 exceeds the width of inner tube 16 at section lines 7—7 of FIG. 5. Therefore, the contact of the hook 46 and taper 48 with inner tube 16 defines the retracted position of needle assembly 14 with respect to inner tube 16. When in such retracted position, the recess 44 is literally within inner tube 16 such that the opening is blocked. This allows retention of the suture as the needle tip 38 penetrates the tissue. The reaction forces from the tissue as the needle tip 38 is being advanced also act to hold needle assembly 14 in the retracted position, as shown in FIG. 5.

As shown in FIG. 5, surface 50 is located more proximally than distal end 18 of inner tube 16. A curved edge 52 is thus formed. The use of the curved edge is necessitated by the expansion of profile of the distal end 32 at surfaces 40 and 42. In order to allow retraction of distal end 32 sufficiently into inner tube 16 so as to close the recess 44, the opposite end of inner tube 16 needed to be cut away back to surface 50. It should be noted that there is a close fit between curved surface 52 and the distal end 32 of needle assembly 14. This may include a small step since curved surface 52 rides above distal end 32. Alternatively, distal end 32 can be thickened so that on retraction of needle assembly 14, the distal end 32 abuts edge 52 so that a smooth surface is presented to avoid trapping any tissue during the procedures involving the apparatus A.

Referring now to FIG. 2, the overall shape of the distal end 18 of inner tube 16, as well as needle assembly 14, is illustrated. As shown in FIG. 2, there is a curvature 54 to improve visibility and ease the suturing process while using the apparatus A. The profile of the inner tube 16 during this curved portion 54 is preferably round. Toward the distal end 18 of inner tube 16, the profile transitions to flat at point 28 (see FIGS. 2 and 3).

It is desirable to keep the suture (not shown) firmly ensconced within the recess 44 as the apparatus A is being withdrawn from the tissue. This pulling force on the apparatus A via handle 2 can have a tendency to make the distal end 32 disengage from the distal end 18 of inner tube 16. Should there be any extension of the needle assembly 14 with respect to inner tube 16, the recess 44 would become exposed, thus releasing the suture. This would be extremely undesirable. To counteract such a possibility, a positive lock assembly L (see FIG. 8) is provided within handle 2. As previously stated, handle 2 has a switch 6 which is connected to a push block 4. Needle assembly 14 is formed into a loop 56 through which extends push block 4. One component of loop 56 is extension member 58. Extension member 58 is cantilevered and is doubled over at point 60 for additional strength. The member 58 is bent so that it rides on the inside wall 62 of handle 2 where it necessarily runs into detent 64. With the cantilevered end 60 abutting detent 64, further extension of needle assembly 14 with respect to inner tube 16 is impeded. However, if a sufficient force is placed on thumb switch 6, which is in turn transmitted to push block 4, push block 4 continues to move and starts to bear on inclined extension member 58. Since the path of push block 4 is predetermined because it moves in a slot (not shown) aligned with the longitudinal axis of handle 2, there comes a time when a sufficient force is transmitted through push block 4 to bear on extension member 58 and begin to deflect it angularly about point 66. Eventually, sufficient angular movement results so that end point 60 is moved around detent 64, allowing further extension of needle assembly 14 with respect to inner tube 16. As long as the surgeon grips the handle 2 without moving switch 6, while he is removing the apparatus A, any tendency of needle assembly 14 to pull out of inner tube 16, thus releasing the suture (not shown), will be resisted by the interaction of end 60 of member 58 against detent 64.

The apparatus of the present invention has several advantages over those of the prior art. The distal extremity of the needle assembly 14 is flat and thin, and the distal end 18 of the housing is flat, thus presenting a low profile. The housing then transitions at 28 to a rounded profile. Rigidity is maintained by the stiflenet tube 20. The sharp edges 34 and 36 allow easy penetration into tissue, minimizing potential trauma. The similar flat profiles presented by the distal end 32 of the needle assembly 14, as well as the distal end 18 of inner tube 16, eliminate irregular surfaces which could cause tissue trauma. The recess 44 is enclosed within inner tube 16 to avoid presentation of notches which could tear the tissue upon movement of the apparatus A. The sharp edges 34 and 36 make precision entry into the tissue possible, while the rapid transition to a rounded profile stretches the tissue, avoiding further tissue trauma. The curved segment 54 promotes visibility and ease in suturing when using the apparatus A. Accidental release of the suture is prevented due to the lock mechanism L shown in FIGS. 8 and 9. The relative movement of the needle assembly 14 with respect to inner tube 16 is controlled in both extension and retraction. Since the distal end 32 of the needle assembly 14 has a greater profile than the distal end 18 of inner tube 16, inner tube 16 effectively acts as a travel stop upon retraction. On extension, the push block 4 engages the proximal end of loose tube 24, as shown in FIG. 8, to prevent further outward movement.

The foregoing disclosure and description of the invention are illustrative and explanatory thereof, and various changes in the size, shape and materials, as well as in the details of the illustrated construction, may be made without departing from the spirit of the invention.

I claim:

1. An apparatus for endoscopic suturing, comprising:

a handle;

an elongated housing extending from said handle having breadth least one side surface;

needle means retractably mounted and extending beyond said housing for penetration into body tissue and for selective retention of a suture against said housing;

said needle means having at least one edge surface; a portion of said needle means having a breadth at least as large as the breadth of said housing, whereupon when said needle means is retracted toward said housing, it cannot be fully drawn into said housing; and said at least one edge surface of said needle means positioned in substantial alignment with said side surface of said housing, to present a smooth transition therebetween when said needle means is retracted toward said housing.

2. The apparatus of claim 1, wherein:

said housing is tubular;

said needle means extends through and beyond said housing.

3. The apparatus of claim 1, further comprising:

switch means on said handle to selectively extend and retract said needle means with respect to said housing;

lock means on said switch means to prevent extension of said needle means out of said housing as the apparatus is withdrawn from tissue while engaging a suture.

4. The apparatus of claim 3, further comprising:

means for defeating said lock means selectively operable by actuation of said switch means.

5. The apparatus for endoscopic suturing of claim 1, further comprising: switch means on said handle to selectively extend and retract said needle means with respect to said housing; and lock means internally of said handle and operably connected to said switch means for automatic retention of said switch means within said handle once said switch means is moved into position retracting said needle toward said housing.

6. An instrument comprising:

a handle;

a housing mounted to said handle and having a breadth, distal and proximal ends at least one side surface;

a needle mounted within and extending distally from said housing;

a suture having a plurality of ends;

means on said needle to accept said suture intermediate its ends; said needle selectively retractable toward said housing for retaining said suture between said housing and said needle, as said handle is moved with respect to body tissue;

said needle having at least one edge surface;

a portion of said needle having a breadth at least as large as the breadth of said housing, whereupon when said needle is retracted within said housing, it cannot be fully drawn into said housing; end said at least one edge surface on said needle positioned in substantial alignment with said side surface of said housing, to present a smooth transition therebetween when said needle is retracted toward said housing, 7. The instrument of claim 6, comprising:

means to retain said needle in a retracted position while the instrument is pulled through tissue by said handle, thereby securing the suture;

switch means on said handle operatively engaged to said means to retain for selective defeating thereof to allow extension of said needle with respect to said housing for release of said suture.

8. A method of endoscopic suturing comprising the steps of:

extending from a housing a needle having a breadth over at least a portion thereof at least as small as said housing;

trapping a suture with a hook formed on said needle by retracting said needle towards said housing;

placing at least one edge located on seed needle in close alignment with at least one side surface on said housing, by virtue of seed retracting, to form a smooth transition; and moving said housing and needle with said trapped suture with respect to the tissue.

9. The method of claim 8, wherein said trapping step further comprises:

moving an open segment of said hook within said housing.

10. The method of claim 9, further comprising:

presenting a smooth transition between said needle and said housing upon trapping said suture for minimizing tissue trauma during said suturing by providing both said needle and said housing with substantially aligned profiles at said transition.

11. The method of claim 10, further comprising the steps of:

actuating said needle by a switch on a handle mounted with said needle;

latching said needle in a retracted position to avoid accidental release of a suture;

selectively overcoming said latching to allow said needle to disengage the suture.

* * * * *

UNITED STATES PATENT AND TRADEMARK OFFICE
CERTIFICATE OF CORRECTION

PATENT NO. : 5,474,565
DATED : December 12, 1995
INVENTOR(S) : A. Frank Trott

It is certified that error appears in the above-indentified patent and that said Letters Patent is hereby corrected as shown below:

At column 5, line 40, please delete "breadth" and insert --a breadth and at-- therefor.

At column 6, line 26, please delete "within" and insert --towards-- therefor.

At column 6, line 27, please delete "end" and insert --and-- therefor.

At column 6, line 48, please delete "seed" and insert --said-- therefor.

At column 6, line 50, please delete "seed" and insert --said-- therefor.

Signed and Sealed this

Thirtieth Day of April, 1996

Attest:

BRUCE LEHMAN

Attesting Officer     Commissioner of Patents and Trademarks